United States Patent [19]

Fong et al.

[11] Patent Number: 5,328,848
[45] Date of Patent: Jul. 12, 1994

[54] METHOD FOR HYDRATING AND CALIBRATING A STERILIZABLE FIBER-OPTIC CATHETER

[75] Inventors: Conrad T. O. Fong, Redmond; Mohamed R. Ali Elmesai, Bellevue; Bruce Q. Fieggen, Snohemish, all of Wash.

[73] Assignee: Abbott Laboratories, Abbott Park, Ill.

[21] Appl. No.: 742,627

[22] Filed: Aug. 8, 1991

Related U.S. Application Data

[60] Continuation-in-part of Ser. No. 324,187, Apr. 14, 1989, abandoned, which is a division of Ser. No. 224,425, Jul. 25, 1988, Pat. No. 4,863,016.

[51] Int. Cl.[5] ............................................. G01N 31/00
[52] U.S. Cl. ............................................. 436/11; 436/8; 436/16; 436/18; 436/68; 252/408.1
[58] Field of Search ........................................ 436/8–19, 436/68; 252/408.1

[56] References Cited

U.S. PATENT DOCUMENTS

| | | | |
|---|---|---|---|
| 3,681,255 | 8/1972 | Wilfore | 436/11 |
| 4,116,336 | 9/1978 | Sorenson et al. | 436/11 X |
| 4,289,648 | 9/1981 | Hoskins et al. | 436/11 X |
| 4,469,792 | 9/1984 | Simmonds et al. | 436/11 |
| 4,711,852 | 12/1987 | Jacobson et al. | 436/8 X |
| 5,012,809 | 5/1991 | Shulze | 128/634 |
| 5,013,666 | 5/1991 | Chiang | 436/11 |
| 5,045,529 | 9/1991 | Chiang | 436/11 X |

Primary Examiner—James C. Housel
Assistant Examiner—Maureen M. Wallenhorst

[57] ABSTRACT

The present invention provides an aqueous buffer solution and method and solution for hydrating and calibrating a sensor membrane of a fiber-optic catheter useful for measuring an analyte other than chloride in a physiological milieu. The temperature, gaseous atmosphere, and aqueous buffer solution of the sensor component are controlled throughout the calibration process in order to ensure that the device is calibrated in accordance with its intended use. The solution is chemically compatible with the intended use of the device and provides compensation for evaporative loss, contaminants, or changes in the solution occurring during storage especially in plastic containers.

12 Claims, 7 Drawing Sheets

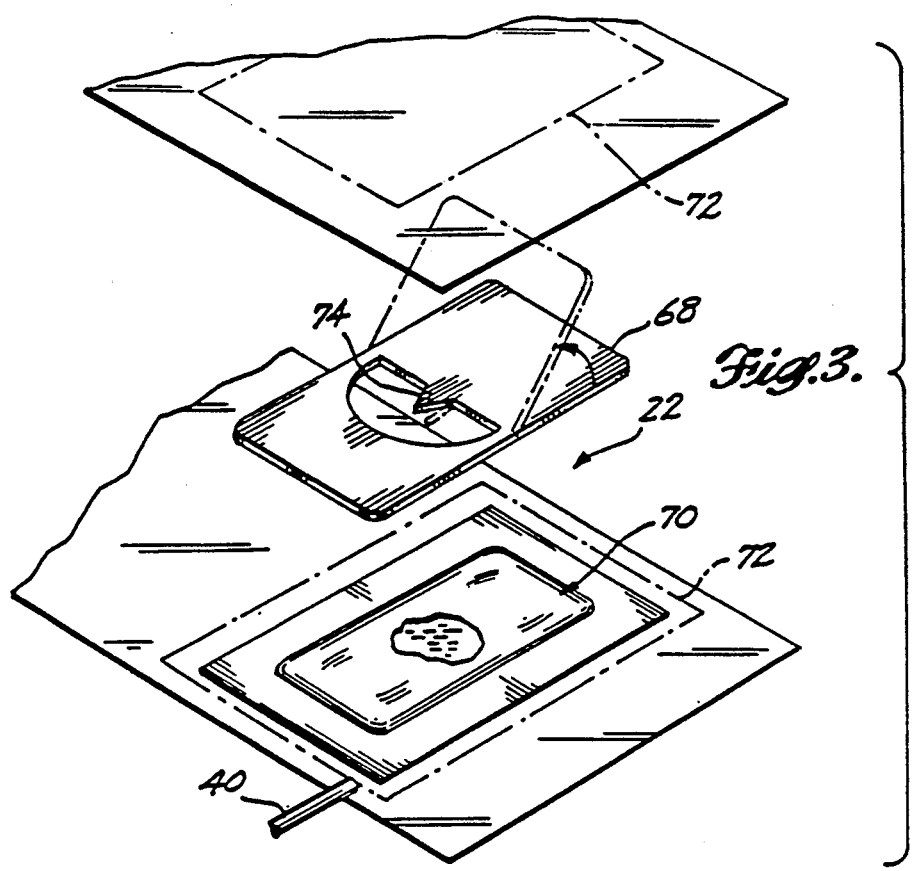
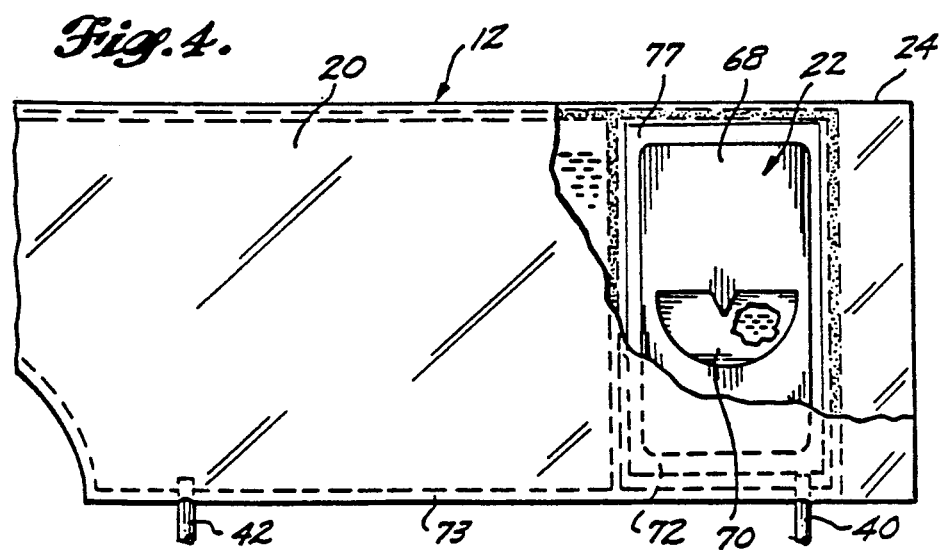

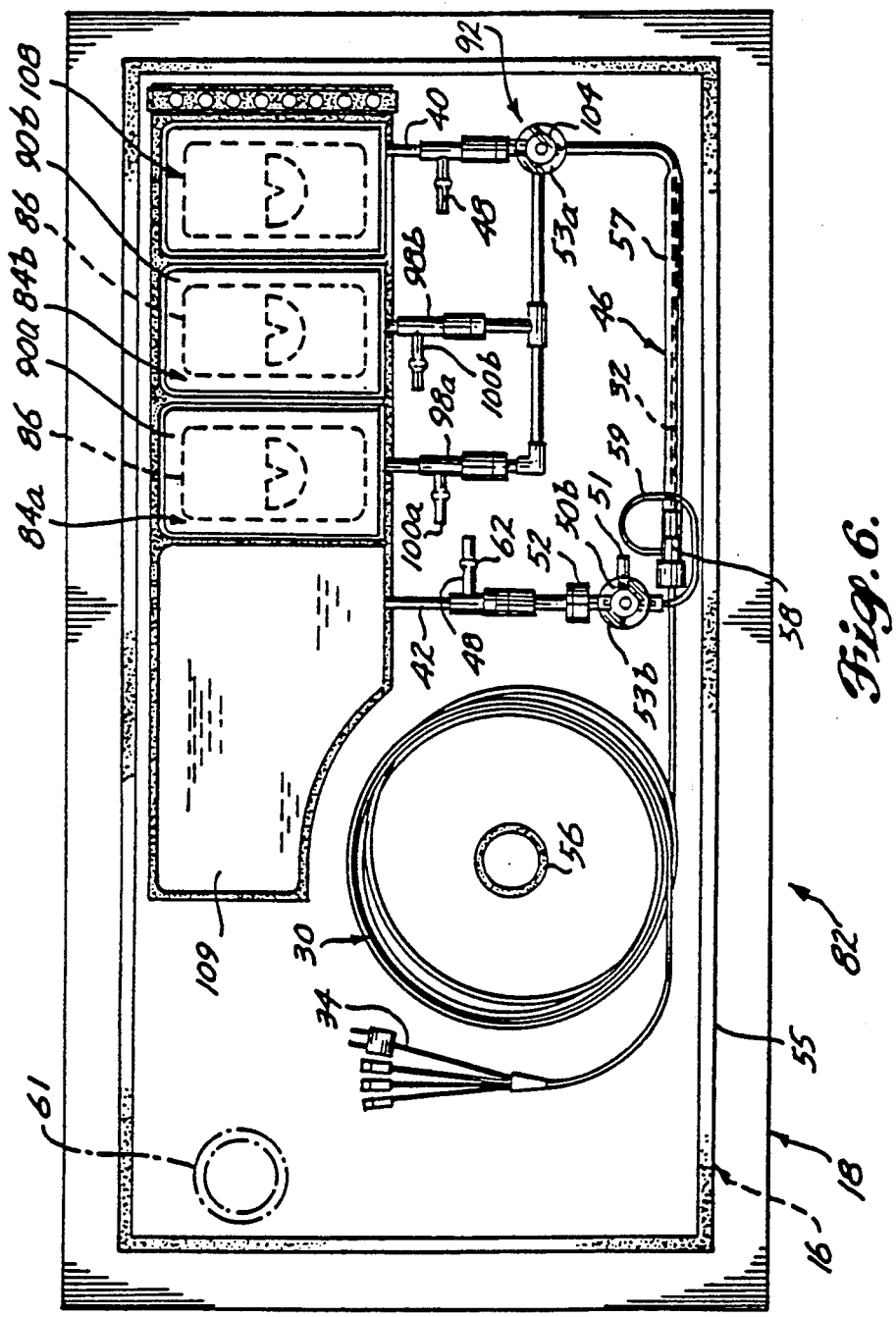

METHOD FOR HYDRATING AND CALIBRATING A STERILIZABLE FIBER-OPTIC CATHETER

This application is a continuation-in-part of Ser. No. 07/324,187, filed Apr. 14, 1989, (now abandoned), which was a divisional application of Ser. No. 07/224,425, filed Jul. 25, 1988 (now issued on Sep. 5, 1989, as U.S. Pat. No. 4,863,016), the benefit of the filing date of which is hereby claimed under 35 U.S.C. §120.

TECHNICAL FIELD

This invention relates to methods of calibration of medical devices consisting of hydratable sensor components.

BACKGROUND OF THE INVENTION

Packages for and methods of packaging medical devices are numerous. The choice of method for packaging a device depends in part on the intended use of the device. Factors include whether the device is used in a sterile environment, whether the device is used in contact with or inserted into a living animal, whether the device is disposable, etc. Certain devices must be sterilized prior to use. One known method for packaging a sterile device is to first insert the device into a gas-impermeable wrap. The interior of the wrap, including the device, is then sterilized. The wrap is then sealed so that the device remains sterilized until the package is opened just prior to use. Once the package is opened, a minimum amount of handling is desirable to avoid the possibility of contaminating the device.

Certain medical devices additionally require calibration prior to use. Medical devices that monitor analyte levels, temperature, etc., often include chemical or electrical sensing components that are very sensitive to temperature, moisture, etc. These devices are generally used in conjunction with monitoring instrumentation that controls and records the monitoring process. For example, a medical device may be connected to a computerized controller which initiates and transmits an electrical or optical signal to the device, receives a resultant signal from the device, and analyzes the resultant signal to produce a value indicative of the measured characteristic.

One common way of calibrating a medical device used for monitoring analyte concentrations is to immerse the sensing component of the device into a calibration solution containing a known amount of the targeted analyte. Base measurement levels are recorded in accordance with the known amount of the analyte. Such calibration solutions must be highly uniform to provide consistent and useful results in the calibration process. The solutions are typically unstable and are only prepared as needed or prepackaged in glass ampules. Glass ampules require especially careful handling during the calibration process to avoid breakage. Shelf life problems, e.g., change of chemistry, separation, etc., may be encountered with prepackaged solutions that are stored over a period of time prior to use. Conventional calibration procedures are time-consuming, costly, subject the device to possible contamination, and often require the presence of a trained technician to oversee the process. Additionally, if a calibratable device is to be stored over a period of time, the device is most easily stored in a dry state to avoid problems arising from the storage of a moist device. Bringing the sensing component of the device from a dry to a functional state often requires hydrating the sensing component over an extended period of time.

When a device must be sterilized as well as calibrated, additional problems arise due to the fact that the sterilization and calibration procedures are often incompatible. For example, one common method of sterilizing a medical device is to expose the device to ethylene oxide (ETO). The ETO procedure is carried out in a non-liquid, i.e., dry, environment. This dry state renders the sensing component of the device completely nonfunctional if the component is meant to operate in a moist environment. In contrast, as discussed above, the common method of calibrating such a device is to immerse the device in a calibration solution. Thus, an ETO sterilization procedure and a moist calibration procedure must be distinct phases in the preparation of the device.

In recent years, optical fiber sensors, also known as optrodes, have been developed to detect the presence of and to continuously monitor the concentration of various analytes, including oxygen, carbon dioxide, glucose, inorganic ions, and hydrogen ions, in solutions. An example of such a sensor is a blood gas sensor for monitoring pH, $pCO_2$, or $pO_2$. Such a blood gas sensor is based on the recognized phenomenon that the absorbance or luminescence of certain indicator molecules is specifically perturbed in the presence of certain analytes. The perturbation in the absorbance and/or luminescence profile is detected by monitoring radiation that is reflected or emitted by the indicator molecule when it is in the presence of a specific analyte. The targeted analyte is generally a part of a solution containing a variety of analytes.

Optrodes have been developed that position an analyte-sensitive indicator molecule in the light path at the end of one or more optical fibers. This fiber unit is often termed the sensor component. The sensor component is an integral part of a blood gas catheter. The indicator molecule is typically housed in a sealed chamber at the end of the fiber(s). The chamber is secured to the optical fiber by a suitable cement material. The walls of the chamber are permeable to the analyte. The sensor component is inserted into and left in a patient for an extended period of time. Analyte readings in the form of optical signals are transmitted from the sensor component to monitoring instrumentation which analyzes the signals and controls the monitoring process.

The sensor component in a blood gas catheter thus typically includes a membrane material, an analyte sensing material, an optical fiber, and a cement. Each element is chosen to be compatible with the other elements and with the monitoring process. In order to monitor a specific analyte, the sensor component is sterilized and then brought to a functional state in which the catheter sensor is responsive to the targeted analyte. Additionally, the monitoring instrumentation is calibrated in conjunction with the specific catheter prior to use. A traditional method for calibrating the monitoring instrumentation involves immersing the catheter sensor component in a calibration solution that has been pre-calibrated to a given set of values, confirmed using a separate calibration instrument such as a blood gas analyzer. If the catheter is subject to the above-described ETO sterilization and packaging process, the analyte sensing material of the sensor is completely dried and is not in proper chemical balance to carry out the monitoring process. Thus, the sensor must be hydrated and calibrated prior to use. If the traditional calibration method described above is carried out, the catheter is exposed and may be contaminated. It is also undesirable for a user to maintain a blood gas analyzer (BGA) for confirming the calibration of a blood gas catheter. Thus, it would be highly desirable to be able to supply a user with a sterile calibration solution and a procedure for using that solution to achieve more than one pre-determined calibration value that can be routinely applied without the requirement for confirming the calibration values in a blood gas analyzer. Further, it would be desirable if: a) the pH of this calibration solution in its packaged form be non-deleterious to the a sensor component stored in the solution; b) the calibration solution was buffered to offset any environmental contaminants that might alter the pH; and, c) if the pH could be brought within the desired range of pH within a reasonable period of time such that the user is not required to wait an inordinate amount of time before commencing use of the blood gas catheter. It would be further advantageous if the calibration solution could be used for hydrating, as well as calibrating, the sensor component of the blood gas catheter.

The package, calibration solution, packaging, and calibration method in the present invention overcomes these and other problems in the prior art.

SUMMARY OF THE INVENTION

The present invention provides a method of hydrating a sensor membrane and calibrating the sensor component and monitoring instrumentation of a fiber optic catheter useful for measuring at least one analyte other than chloride in a physiological milieu to determine pH, $pO_2$ or $pCO_2$ and this is accomplished without a requirement for additional calibration instrumentation. the method involves hydrating and calibrating the sensor membrane in a preparation solution that includes an amount of an anion that is substantially equivalent to the level of the predominant anion at the point of use, i.e., in the composition of the physiological milieu including the targeted analyte. The predominant anion is different from the targeted analyte. The inclusion of the predominant anion in the preparation/calibration solution reduces the ionic gradient across the membrane and reduces measurement errors that result from evaporative loss of water from the preparation/calibration solution. The solution allows a blood gas catheter to be calibrated immediately prior to use without the need for calibration instrumentation, e.g., a blood gas analyzer.

The invention provides a user with a sterile calibration solution and a procedure for using that solution to achieve more than one pre-determined calibration value. This is accomplished by gassing the solution under controlled atmospheric conditions so that the desired calibration values can routinely be achieved without the requirement for confirming the calibration values in a blood gas analyzer. Further, the invention provides that: a) the pH of the preparation solution in its packaged form is not deleterious to a sensor component stored in the solution; b) the calibration solution is buffered to offset any environmental contaminants that might alter the pH, i.e., such as ETO residual compounds created during ETO sterilization procedures; and, c) the pH, although well buffered, can still be gassed to the desired range of pH within a reasonable period of time such for a user. The preparation solution can also be used for hydrating, as well as calibrating, the sensor component of the blood gas catheter.

A further aspect of the present invention is a kit for hydrating a sensor membrane of a fiber optic sensor membrane of a fiber-optic catheter for measuring pH, $pO_2$ or $pCO_2$. The kit includes a sensor membrane, the preparation/calibration solution, and the instructions for hydrating and calibrating the sensor membrane of the fiber-optic catheter.

BRIEF DESCRIPTION OF THE DRAWINGS

FIG. 3 is an exploded isometric view of a solution reservoir in accordance with the present invention;

FIG. 4 is a top perspective view of a manifold in accordance with the present invention;

DETAILED DESCRIPTION OF THE PREFERRED EMBODIMENTS

Figure 1:
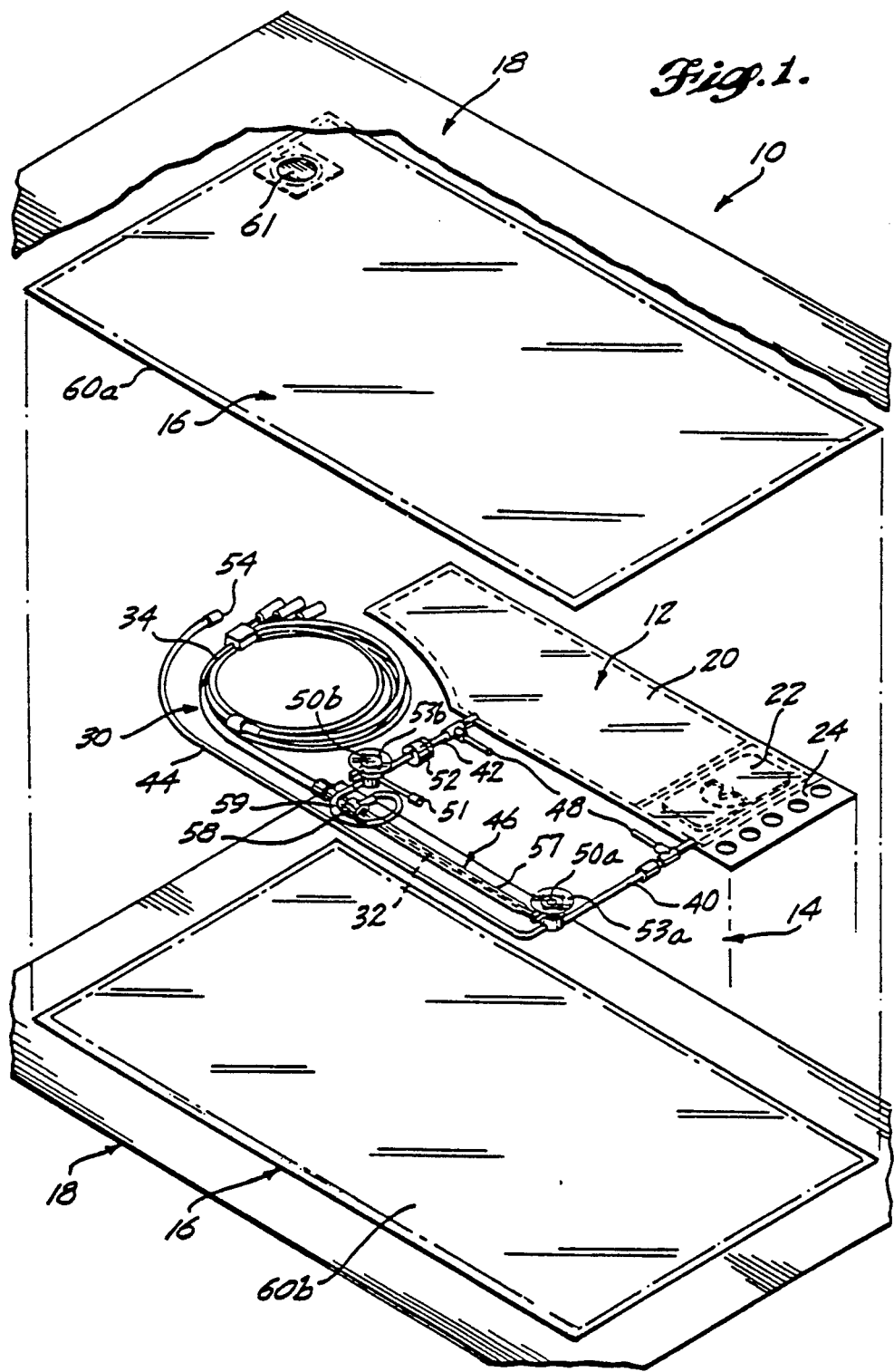
FIG. 1 is an exploded isometric view of a package in accordance with the present invention.

With reference to FIG. 1, one preferred embodiment of package 10 includes manifold 12, plumbing 14, inner wrap 16, and outer wrap 18. The manifold includes deposit reservoir 20, hydration reservoir 22, and flap 24. The deposit reservoir 20 and hydration reservoir 22 are connected to a medical device such as catheter 30 by plumbing 14. The plumbing is connected to the catheter at the sensor component 32 which includes the analyte sensing components of the catheter. The sensor component may also include a temperature measuring component. The sensor component 32 is disposed within the plumbing. The catheter also includes one or more instrumentation cables 34 which ultimately connect the catheter 30 to the remainder of the medical monitoring device (not shown). The sensor component extends from the cable 34. At the sensor-cable connecting point, a cable flange (not shown) extends radially from the cable.

The plumbing 14 includes hydration tube 40, flush tube 42, calibration tube 44, delivery device 46, sterilization tubes 48, stopcocks 50a and 50b, gas filter 51, and directional valve 52. Preferably, all of the tubing in plumbing 14 is polyvinyl chloride (PVC) tubing. Such tubing is easy to handle and is slightly gas-permeable over an extended period of time.

The stopcocks 50 are three-way adjustable valves. The settings of the stopcocks are manually adjustable and are easily manipulated through the packaging materials. The stopcocks are used to control the flow of solution through the plumbing. Caps 53a and 53b overlay the stopcocks in order to protect the packaging material from damage caused by protrusions on the stopcocks.

Hydration tube 40 is in full communication with hydration reservoir 22, a sterilization tube 48, and stopcock 50a. Flush tube 42 is in full communication with the deposit reservoir 20, a sterilization tube 48, and directional valve 52. Directional valve 52 allows solution to flow through flush tube 42 into the deposit reservoir and prevents solution flow in the opposite direction. Calibration tube 44 is in full communication with filter 54 and stopcock 50a. Filter 54 is preferably a hydrophobic filter through which gaseous solutions freely pass and which prevents the passage of liquid solutions.

Delivery device 46 includes catheter tube 57, joint 58 and connect tube 59. One end of catheter tube 57 is connected to stopcock 50a. The other end of the catheter tube is connected to joint 58. Joint 58 connects catheter tube 57, connect tube 59 and cable 34. The connect tube is connected to stopcock 50b. The joint provides fluid communication between the catheter tube and the connect tube. Delivery device 46 is preferably used to deliver the sensor component to the patient, i.e., the delivery device is an integral component of the blood gas catheter. Thus, the materials used for delivery device 46 are compatible with the packaging procedure as well as with the blood gas monitoring procedure.

The sensor component extends from cable 34, through joint 58 and into catheter tube 57. The joint includes a ring seal (not shown) through which the sensor component extends and against which the cable flange is pressed. The ring seal and flange prevent the flow of solution from the joint to the cable. The position of the cable and sensor component relative to the joint is fixed by a suitable attachment mechanism such as a nut screwed over the joint and against the flange. In this manner, any fluid flowing between stopcock 50a and 50b passes over the sensor component.

Stopcock 50b is connected to filter 51 and directional valve 52. Filter 51 is preferably a hydrophobic filter through which gaseous solutions freely pass and which prevents the passage of liquid solutions.

The plumbing establishes gaseous communication between the sensing component and the plumbing ambient environment by means of sterilization tubes 48, filter 51, and filter 54. The plumbing also establishes liquid communication between the manifold reservoirs and the sensor component by hydration tube 40, delivery device 46, and flush tube 42.

Inner wrap 16 includes sides 60a and 60b. Side 60a includes filter 61 along one edge. The filter 61 is preferably a bacterial retentive hydrophobic filter. An exemplary filter 61 is a fibrous paper-like membrane manufactured by E. I. DuPont de Nemours & Co. and referred to by the trademark TYVEK. The filter allows gas exchange between the interior and exterior of inner wrap 16 when the wrap is otherwise sealed in a gas-impermeable manner. The remainder of the material of side 60a is preferably clear so that the packaging is easily viewable therethrough. The material is also relatively thin and flexible so that the adjustments to the packaging, e.g., the stopcocks, are easily carried out through the wrap.

Figure 2:
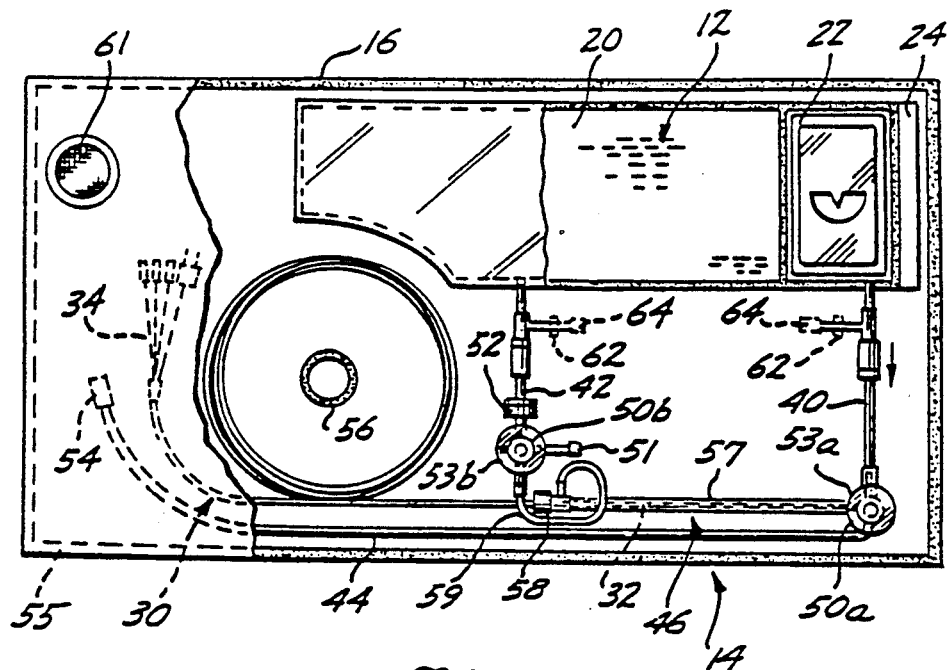
FIG. 2 is a top perspective view of a package in accordance with the present invention.

During the packaging process, catheter 30 is sterilized dry, and then hydrated and prepared for calibration. With reference to FIG. 2, hydration reservoir 22 and deposit reservoir 20 are connected to catheter 30 at sensor component 32 by plumbing 14. These components are placed between the sides 60a and 60b of inner wrap 16 and the outside edges of the inner wrap are completely sealed by edge seals 55. Flap 24 of the manifold is caught between the edge seals to secure the position of manifold 12 within inner wrap 16. Additionally, seal 56 preferably secures the position of catheter 30 within the inner wrap by securing the gathered cable 34. The manifold 12 and catheter 30 are positioned within the inner wrap so that plumbing 14 is and remains untangled relative to the catheter, and so that access to filter 61 is not blocked. Once the inner wrap edges are sealed, filter 61 is the only means of gaseous communication between the interior and the exterior of the wrap.

Prior to the sterilization process, stopcocks 50 are open so that the lumens of the hydration tube, calibration tube, catheter tube, connect tube, and flush tube are all in fluid communication. In order to sterilize the catheter, sealed inner wrap 16 functions as a breather bag. The wrap is simply a gas-permeable container which acts to keep the gaseous environment within it free from bacteria and germs. A sterilizing gaseous solution, preferably ethylene oxide (ETO), is pumped into inner wrap 16 through filter 61. This is performed by pressurizing the atmosphere surrounding inner wrap 16. The ETO flows freely over catheter 30, plumbing 14 and manifold 12. Additionally, the ETO flows into plumbing 14 through sterilization tubes 48, filter 51, and filter 54. In this manner, sensor component 32 and the interior surfaces of the plumbing and the manifold are sterilized. After sterilization, the ETO is outgassed from inner wrap 16 by allowing the inner wrap to stand and the ETO to dissipate in a controlled environment.

Preferably, all surfaces and passageways of manifold 12, plumbing 14, and catheter 30 are sterilized during the ETO procedure. Certain joints and attachments in plumbing 14 may be so tight that they are essentially ETO impermeable and therefore hinder or restrict access of ETO. These joints and attachments are loosened prior to the sterilization procedure and are tightened immediately thereafter.

After sterilization, sterilization tubes 48 are sealed with seals 62 (shown in reference). Preferably, tubes 48 are sealed by a radio frequency (RF) sealing technique. This technique affects a heat seal without affecting the integrity of inner wrap 16. After seals 62 are in place, the only points of entry remaining in plumbing 14 are through manifold 12 via hydration tube 40 and flush tube 42, filter 51, or through filter 54. Alternatively, sterilization tubes 48 include filters 64 (shown in reference). Filters 64 are preferably hydrophobic filters which allow gaseous solutions to pass freely through, but liquid solutions, such as the hydration solution, are not allowed to pass through. If such filters are used, the sterilization tubes 48 do not require sealing after the sterilization process.

During the foregoing ETO sterilization procedure, the surfaces exposed to the ETO are completely dried. Thus, sensor component 32 is rendered nonfunctional since it operates in a moist environment. Sensor component 32 must be hydrated after sterilization and prior to use. Manifold 12 and plumbing 14 are used to hydrate the sensor component without removing it from its sterile environment within inner wrap 16.

In order to hydrate sensor component 32 within the sterile environment of inner wrap 16, a hydration solution is included within the inner wrap. The hydration solution is held and protected throughout the sterilization procedure in hydration reservoir 22. After sterilization, the hydration solution is released from hydration reservoir 22. Manifold 12, in conjunction with plumbing 14, delivers the hydration solution to sensor component 32 which is the portion of catheter 30 which requires hydration to be functional. The remainder of the catheter is maintained in a dry state.

With reference to FIG. 3, one preferred hydration reservoir 22 includes rupture plate 68, container 70, and outer envelope 72. Container 70 is suitable for holding a liquid such as a hydration solution or calibration solution. Container 70 protects the solution from contact with the ETO which is highly toxic. The container material is impermeable to ETO and is capable of withstanding the pressure and temperature changes that occur during a standard ETO sterilization process. In this manner, the solution is maintained in a sterile and nonpyrogenic state. Additionally, the container material is rupturable by mechanical pressure as will be discussed below. One suitable material for container 70 is foil-polypropylene laminated film.

Rupture plate 68 is preferably made up of a relatively rigid material. The plate is flat and corresponds in surface area to the surface of container 70. The rupture plate includes point 74 which, under adequate mechanical pressure, turns downwardly towards container 70 to rupture the container. The rupturing position is shown in reference.

With reference to FIG. 4, outer envelope 72 is formed about container 70 and rupture plate 68 so that there is adequate room within the envelope for the solution to flow from the container into the envelope and to hydration tube 40. Envelope 72 and deposit reservoir 20 are preferably made from two pieces of material that are connected by seals 73 (shown in reference) so that deposit reservoir 20, envelope 72, and flap 24 are formed. Container 70 is configured so that the container does not block the hydration tube when sealed within envelope 72. Flat edges 77 along the perimeter of container 70 aid in this positioning. Hydration tube 40 and flush tube 42 are sealed in communicating relationship with the interior of envelope 72 and the interior of deposit reservoir 20, respectively.

Referring again to FIG. 2, in order to hydrate sensor component 32, stopcock 50a is adjusted so that the fluid path between hydration tube 40 and catheter tube 57 is open. Stopcock 50b is adjusted so that the fluid path between connect tube 59 and valve 52 is open. Container 70 is ruptured as discussed above. The contents of the container are forced into envelope 72 by applying uniform pressure to rupture plate 68 against the container. The hydration solution flows through envelope 72 and hydration tube 40 to delivery device 46. Once the delivery device is filled with hydration solution, stopcocks 50a and 50b are adjusted in order to close off the delivery device thereby securing the solution over sensor component 32. The solution is held there in order to adequately hydrate the sensor component. Preferably, some of the hydration solution is held in the delivery device during the storage period, i.e., until calibration takes place. In this manner, sensor component 32 is held in a hydrated state during the storage period.

Preferably, the hydration fluid contains a chemical composition the same or very close to the composition contained in the initial calibration solution to be used with the device. Each solution content is highly sensor specific. The hydration solution may be formulated to also act as a calibration solution and be used to establish a first calibration point of the sensor component, e.g., by equilibrating the hydration-calibration solution with gases at levels appropriate for calibration of the specific analyte sensor in sensor component 32.

After sensor hydration has taken place, catheter 30 is preferably incubated to aid in returning the catheter to a functional state, and to stabilize the sensor component chemistry. Sensor component 32 is incubated in the hydration solution that is held within catheter tube 57. To ensure the chemical balance of the solution is held constant, the package itself is incubated in a gas controlled environment. Inner wrap 16 is placed in a gas-impermeable container and flushed with a gaseous solution. The gaseous solution in which the inner wrapper and contents are incubated has chemical characteristics that are essentially the same as those of the dissolved gases in the hydration solution. The gaseous solution is also pre-equilibrated with water, i.e., the solution is hydrated. This characteristic of the gaseous solution prevents the solution from drawing the water off of the hydration solution held within delivery device 46. The gaseous solution passes through filter 61 into the interior of the inner wrap. Because of this controlled environment external to plumbing 14, no change in the chemical composition of the hydration solution will be affected due to the slight gas-permeability of delivery device 46. The dissolved gases in the hydration solution are thus maintained at the desired level. The time period, temperature, and gaseous composition for incubation are highly dependent on the sensor component elements and intended use.

For storage purposes, the gas-permeable portions of inner wrap 16 are sealed off. Preferably, the wrap is placed within outer wrap 18. The outer wrap is gas-impermeable and acts to seal the inner wrap gas-permeable sections including filter 61. Outer wrap 18 creates a constant gaseous environment surrounding catheter tube 57 and sensor component 32. A gaseous solution is pumped into the outer wrap and passes into inner wrap 16 through filter 61. The gaseous solution preferably has similar chemical characteristics to the incubation solution and the hydration solution. Again, the controlled environment ensures that the composition of gases dissolved in the hydration solution will not be altered by gaseous exchange through the delivery device. In this manner, the chemical composition of the hydration solution in the delivery device is maintained at a constant level throughout the storage period. Prior to use, depending upon the specific sensor component, it may be preferable to again incubate the entire package to further enhance the response of the sensor component.

Figure 5:
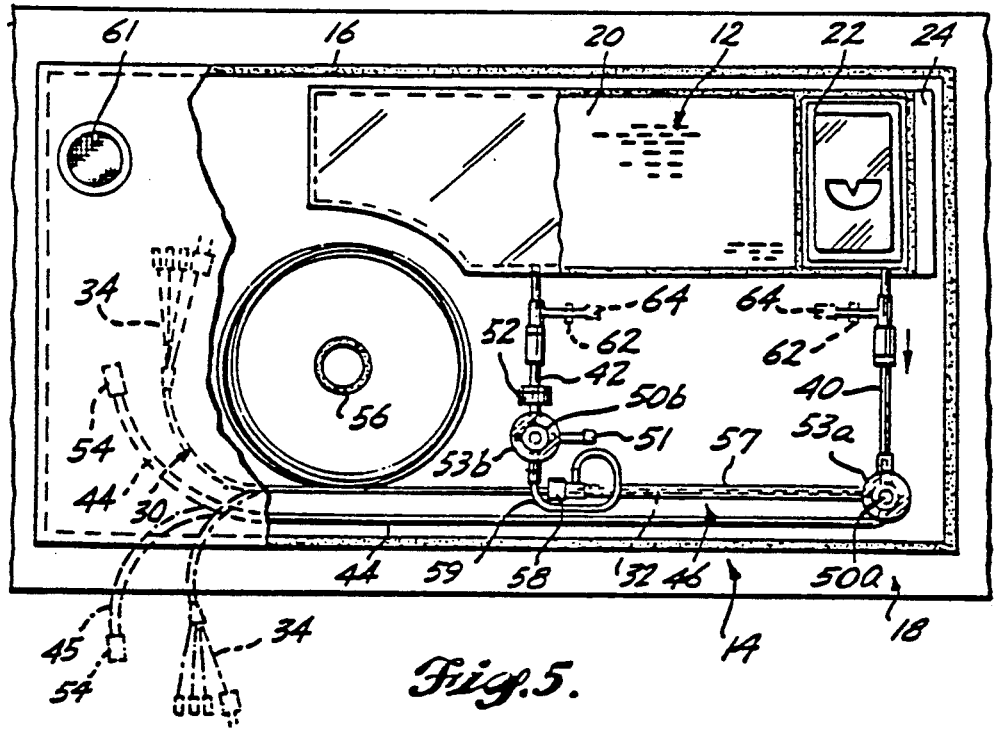
FIG. 5 is a top perspective view of a package in accordance with the present invention with the instrumentation cable of the medical device and the calibration tube of the package exposed in order to calibrate the medical device; and, FIG. 6 is a top perspective view of a medical device sealed in the inner wrap of a package including sterilizable calibration solution reservoirs in accordance with the present invention.

With reference to FIG. 5, calibration tube 44 and cable 34 are removed from both inner wrap 16 and outer wrap 18 at a point remote from the sensor component 32. The cables are connected to monitoring instrumentation (not shown). In this manner, the readings obtained by the catheter 30 are transmitted to the monitoring instrumentation.

Preferably, calibration tube 44 is small-bore tubing that has a small volume. This configuration reduces the amount of fluid that must be displaced when one or more calibration solutions are introduced into the plumbing.

To calibrate the device, two calibration solutions are typically used. Each solution contains a predetermined concentration of the targeted analyte. Filter 54 is removed from calibration tube 44 and an injection device (not shown) is attached thereto. A container of calibration solution is attached to the injection device. The injection device preferably includes a stopcock. The calibration solution passes from the container through calibration tube 44 and stopcock 50a to catheter tube 57 and connect tube 59. Stopcock 50b is set so that the solution flows through the stopcock to deposit reservoir 20 until enough solution from the delivery device 46 has been displaced to ensure that all of the solution held within the delivery device is the first calibration solution. At that point, the stopcock on the injection device is closed to hold the calibration solution within the delivery device.

Preferably, the temperatures of the calibration solution and sensor component are controlled throughout the calibration process. The temperatures are brought to and maintained at a temperature substantially equivalent to the temperature of the point of use of the sensor component, e.g., body temperature for a blood gas catheter. This control ensures that the calibration measurements taken are accurate. The temperature of the calibration solution is adjusted while the solution is in the container prior to delivery to the sensor component. The temperature of the wrap and its contents is adjusted by inserting the wrap between the sides of a thermal blanket. The wrap remains enveloped by the thermal blanket throughout the calibration procedure. In this manner, the sensor component is maintained in its clean environment during the calibration procedure. If the sensor component includes a temperature sensing component, the temperature sensing component is utilized to provide component temperature information.

Once the calibration solution is delivered to the delivery device and the temperature of the sensing component stabilized, analyte measurements are taken via cables 34. Once the measurements are taken, the injection device stopcock is opened and a second solution is transmitted to delivery device 46 in a similar manner. As an alternative method of retaining the hydration solution within the delivery device, stopcocks 50a and 50b are closed to hold the solution therebetween while the calibration measurements are taken.

Once calibration is completed, a parenteral grade saline solution is flushed through the plumbing to wash out any remaining calibration solution. The solution is introduced to the plumbing through calibration tube 44. The catheter is then removed from the package by disconnecting the delivery device from the remainder of the plumbing. The joints at stopcocks 50a and 50b are disconnected and delivery device 46 and sensor component 32 are removed as a unit. The remainder of the package is disposed of.

Since all solutions are flushed into deposit reservoir 20, the reservoir is sized so that its capacity is equal to or greater than the total volume of all of the hydration, calibration, and cleaning solutions to be used to prepare the catheter for use.

With reference to FIG. 6, a preferred package embodiment 82 is similar to package 10, but includes calibration reservoirs 84a and 84b, each containing a separate calibration solution, as well as reservoir 108 containing a hydration solution. (Similar components between packages 82 and 10 will be referred to with the same reference numbers.) The calibration reservoirs are similar to reservoir 22 of package 10. Reservoirs 84a and 84b each include a rupture plate 86, a container (not shown), and an envelope 90a and 90b, respectively. The plumbing 92 includes calibration tubes 98a and 98b, sterilization tubes 100a and 100b, and a passage tube connecting 98a and 98b with stopcock 104. The calibration tubes are connected to the calibration reservoirs along the seals of envelopes 90a and 90b. The calibration tubes are connected to passage tube 102 which is connected to stopcock 104. Stopcock 104 is similar to stopcock 50a. The remainder of plumbing 92 is similar to plumbing 14. The package also includes deposit reservoir 109 sized so as to receive all of the hydration and calibration solutions and any cleaning solutions to be used.

To prepare catheter 30 for use, an ETO sterilization procedure as described above is carried out. Sensor component 32 is then hydrated and incubated. Inner wrap 16 is packaged in outer wrap 18 for storage purposes. Prior to use, cables 34 are removed from the inner and outer wraps and connected to monitoring instrumentation. Calibration reservoir 84a, including the first calibration solution, is ruptured and the solution directed into delivery device 46. The stopcocks are adjusted to hold the solution in the delivery device. The temperature of the sensor component is controlled as described above. Calibration measurements are taken when the temperature of the sensor component is stabilized and correct. Once the first calibration measurement is completed, calibration reservoir 84b, including the second calibration solution, is ruptured and the solution directed into the delivery device. The temperature of the sensor component is again stabilized and corrected. The second calibration point is then established and the catheter is ready for use.

In each of the above-described embodiments, the sensor component may be brought to first calibration point conditions by utilizing a specifically equilibrated hydration solution. The hydration solution is equilibrated with a gaseous composition equivalent to that used to create the first calibration solution. When the first calibration point conditions are achieved in this manner, only one calibration solution, that corresponding to the second calibration point conditions, need be introduced to the sensor component during calibration. This reduces the steps required to prepare the catheter for use. Similarly, if the package is for a medical device that requires the setting of only a single calibration point, then a properly equilibrated hydration solution is the only solution necessary to prepare the device for use. In such an instance, the plumbing need not include a calibration section for delivering calibration solution to the sensor component. To utilize such a device, the instrumentation cables are removed from the packaging and connected to monitoring instrumentation. The sensor component is already immersed in the hydration solution that acts as the calibration solution. Calibration measurements are immediately taken and the device is then ready for use.

As an example of the relationships between the various solutions and the sensor component, if a blood gas catheter were to be used to measure pH, $pO_2$ and $pCO_2$, the buffer formulations for the calibration solutions would be selected to control the relationship between pH and $pCO_2$. Calibration solutions are characterized by their differing $pCO_2$ levels.

The following solution is a specific example of a calibration solution that is suitable for use with the above-described catheter:

0.916 grams/liter potassium phosphate;
3.007 grams/liter sodium phosphate;
6.136 grams/liter sodium chloride; and
1.848 grams/liter sodium bicarbonate.

The solution is a bicarbonate-phosphate buffer which contains 105 mM sodium chloride as a predominant anion, which is the sodium chloride level that is substantially equivalent to that found in blood. The solution is adjusted with carbon dioxide gas and compressed air, or the equivalent oxygen/nitrogen mixture, to form the hydration and calibration solutions having one, two or more desired calibration points.

In a preferred embodiment, it is desirable that the solution be prepared within certain test limits: namely, that the solution (above) as prepared and tested against a standard solution prior to packaging have a chloride ion concentration that falls within a range $+/-3\%$ of the standard solution; sodium ion concentration within $+/-5\%$; and, potassium ion concentration within $+/-5\%$.

A suitable time and temperature for incubation of a blood gas catheter sensor component has been found to be at least 7 days at a temperature of approximately 20° C. This incubation is adequate to bring the sensor component of the catheter to calibration conditions reflected in the amount and type of chemicals included in the gaseous mixture. Prior to use, it is preferable to again incubate the entire package for approximately 7-14 days (but times of up to 30 days are also acceptable) at a temperature substantially equivalent to the temperature at the point of use. For an in situ blood gas catheter, the temperature range for the second incubation is 37° C. to 40° C. The second incubation has been found to improve the pH response time of the catheter. The catheter is then in a state for final calibration and use.

It has been found that the inclusion of sodium chloride in the preparation solutions is useful to reduce perturbations in the measuring process that are caused by the existence of predominant ions other than the targeted analyte(s) in the solution being monitored. In blood, sodium chloride is a predominant ionic compound that is not monitored by the blood gas catheter of the example. If the preparation solutions in which the sensor component is hydrated and calibrated do not contain the chloride component, an ionic gradient is created across the sensor component membrane when the sensor component is actually used in blood. This gradient affects the subsequent monitoring information received from the sensor component. The inclusion of a predominant anion compensates for the ionic gradient across the sensor component so that "defective" preparation solutions can be used to calibrate the sensor component so that it will accurately measure the pH in blood.

The term "defective" as used herein is intended to mean those preparation solutions which would have a differing calibration value, e.g., pH, from the desired calibration value, e.g., pH, if they were measured in a blood gas analyzer.

The term "gassing" a calibration solution to a desired calibration point is intended to mean exposing the aqueous buffer solution in a pre-determined gaseous atmosphere under conditions of controlled temperature and measured barometric pressure for a sufficient time to achieve a desired calibration point, e.g., a desired pH, $pO_2$ or $pCO_2$ calibration value. In preferred embodiments of the invention gaseous atmospheres of nominal 8.3% $CO_2$, 8.3% $O_2$, and 83.4% $N_2$ or 2.8% $CO_2$, 21% $O_2$ and 76.2% $N_2$ are provided, i.e., based on actual tank analysis of the gases and use in a sealed calibration and hydration chamber where there is no difference between the gaseous atmosphere in the chamber and in the tank. Further, it will be recognized by those skilled in the art that other inert gases, e.g., argon, can be readily substituted for nitrogen in the mixture of $CO_2$ and $O_2$.

The term "calibration point" is intended to means a pre-determined value for pH, $pO_2$ or $pCO_2$ that is desirable for calibrating a sensor component and monitoring instrument of a blood gas catheter.

A "defective" preparation solution means an aqueous buffer solution resulting from contamination of the solution with ionic species shifting the chemical equilibria, e.g., during ETO or other chemical or gaseous sterilization procedures, or by evaporative loss of water.

Evaporative loss of water from the aqueous buffer solution of the invention can occur in at least two ways: during storage of the solution at room temperature, and/or during incubation of the solution in a dry gas stream as the sensor component is hydrated and calibrated. Evaporation can cause changes in ion concentration which can cause changes with time in $pO_2$, $pCO_2$, or pH measured in the solution by a BGA. These errors caused by evaporative loss are compounded by individual variations between different packages of calibration solution (or hydration fluid) stored for the same period of time at room temperature. In addition, slight variations in temperature and gas flow rates during the calibration procedure result in individual variations in electrolyte concentration in the calibration solutions used to hydrate and calibrate different individual sensors. Thus, measurements of the absolute values of a "defective" calibration solution in a BGA would suggest that such a solution is not suitable for calibrating the sensor component and monitoring instrumentation of a blood gas catheter, and would lead one to believe that extreme efforts must be made to control evaporative loss, and to standardize the individual variations between different sensor components and different packages of preparation solution. Fortunately, this has not been found to be the case if the preparation solution contains a predominant anion.

It has been found that calibration errors due to evaporative loss in the calibration solution that resulted in measurable changes in the pH of the calibration solution (i.e., when measured in a blood gas analyzer; BGA) were compensated for when calibrating the sensor component of blood gas catheter, by the inclusion of a predominant anion (preferably chloride, because this anion is not measured by the sensor in blood) as part of the chemical composition of calibration solutions described above. Further it was found that calibrating the sensor component and monitoring instrumentation against a "defective" solution gassed to two different calibration points was effective in calibrating the sensor component for use in blood. Thus, the absolute properties of the preparation solution of the invention (as measured in a BGA) did not influence the calibration of the sensor component and monitoring instrumentation and it was possible to ignore the absolute values of the solution as measured in a BGA. The instant invention thus eliminates the need for a BGA to confirm the physical properties of a calibration solution.

The results presented in the Experimental Examples (below) show that increasing the concentration of the electrolytes in the calibration/hydration solution (i.e., to create an artificially "defective" hydration buffer) followed by gassing to achieve two different pre-determined pH calibration points (pH 7.2 and pH 7.6) significantly increased the absolute pH of the solution measured in the BGA. As the concentration of electrolytes was increased by 50%, more than a 0.2 unit pH change was observed, e.g., from a pre-determined value of pH 7.2 up to a value of pH 7.4. The magnitude of the pH change observed in these studies was sufficient to suggest that a sensor calibrated in such a defective calibration solution could not be used to monitor pH in a patient where changes of 0.04 pH units may be highly significant (i.e., if following a consistent pattern of pH change).

Unexpectedly, the results show that sensors calibrated in such defective calibration/hydration solutions that had been driven by gassing to two different calibration points, were properly calibrated when using a calibration solution prepared in accordance with the present invention. The preparation solution of the invention tolerates physical changes (e.g., evaporation) in the buffer concentrations without introducing significant errors in subsequent measurements of pH, $pCO_2$ and $pO_2$ by a sensor component and monitoring instrument calibrated in the solution. While greater scatter was observed in the error values, the values were still within an acceptable range for use in patient monitoring. For example, when a sensor was hydrated and calibrated in buffer prepared to mimic 50% evaporative loss, the pH measurements and error of the sensor were still within acceptable limits. After further experimentation (described below), it appears that the basis for this fortunate result resides in the inclusion of a predominant anion (e.g., chloride anion) in the calibration/hydration solution. Apparently, as the buffer concentration increases (e.g., during evaporative loss), the increasing predominant anion concentration (e.g., chloride) tends to decrease the pH measured by the sensor at the same time that the change in the chemical equilibrium of the phosphate and bicarbonate buffer constituents are tending to increase these values. The BGA measures such changes, but inclusion of the predominant anion in the solution allows the sensor component and monitoring instrumentation of the blood gas catheter to compensate for the changes. Thus, the result of these opposing processes is a net change near zero as measured by the blood gas catheter. The present calibration/hydration solutions and methods allow acceptable hydration and calibration of a blood gas sensor component, e.g., evaporative changes, and while chloride ion is the anion in a preferred embodiment above, it is believed that other anions to which the probes are sensitive will also be useful, and these will vary with the predominant anion in the sample being analyzed by the blood gas catheter. As indicated above, the choice of the anion for use in the preparation solution will require that the anion not be one that will be measured by the sensor, and that the anion be a predominant anion in the solution where the measurements are to be made.

EXPERIMENTAL EXAMPLES

To assess the potential magnitudes of the calibration errors and their effect on pH, $pO_2$, and $pCO_2$ measurements of bicarbonate-phosphate-chloride buffer, compositions were prepared (as above) at pH 7.2 and pH 7.6 and termed NBB1. The pH 7.2 set of buffers was prepared to mimic a pH 7.2 calibration buffer, but at 0.9, 1.0, 1.1, 1.2, 1.3, and 1.5 times (i.e., $0.9\times$, $1.0\times$, etc.) the normal concentration of all components, respectively. The pH 7.6 set of buffers was prepared to mimic a pH 7.6 calibration buffer at the same $0.9\times$–$1.5\times$ concentrations. For pH measurements, each buffer was tested with eight blood gas catheter sensor components pre-calibrated using solutions in which the physical properties were confirmed by testing with a BGA. The solutions were thus BGA-pre-calibrated at either pH 7.2 or pH 7.6, i.e., $1.0\times$ NBB1, pH 7.2 or $1.0\times$ NBB1, pH 7.6, respectively. For these studies, each different buffer composition was placed in a separate multiple probe equilibration vessel (MPEV). For the set of NBB1, pH 7.2 buffers, the MPEVs were flushed under controlled atmospheric pressure (i.e., to gas the calibration solution to the desired calibration point) with a gas mixture of nominal 8.3% $CO_2$, 8.3% $O_2$, and 83.4% $N_2$, and for the set of NBB1, pH 7.6 buffers, the MPEVs were flushed with a mixture consisting of nominal 2.8% $CO_2$, 21% $O_2$, and 76.2% $N_2$. A transfer block containing the eight precalibrated probes was moved between the different MPEVs, allowing approximately 30 minutes for equilibration in each vessel prior to beginning measurements. The measurements were then taken over a period of 20 minutes (allowing for the probe to respond to the new environment) and the average value, standard deviation, and range of values determined. Samples were also removed from the MPEVs and the absolute physical properties were determined by analysis in a BGA.

Figure 7:
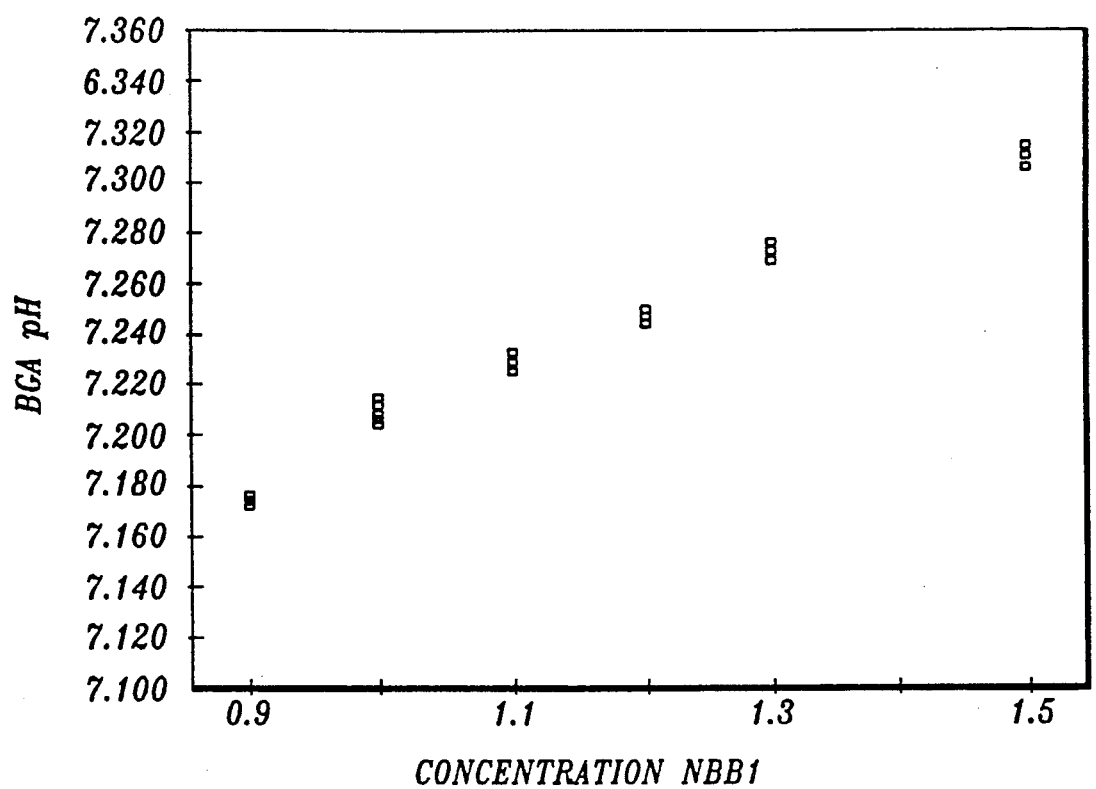
FIG. 7 graphically represents the increase in apparent pH recorded by a blood gas analyzer (BGA) in different concentrations of a "defective" calibration solution, i.e., made up to mimic a pH 7.2 solution that has undergone evaporative loss and thus has experienced an increase in the buffer concentration.
Figure 8:
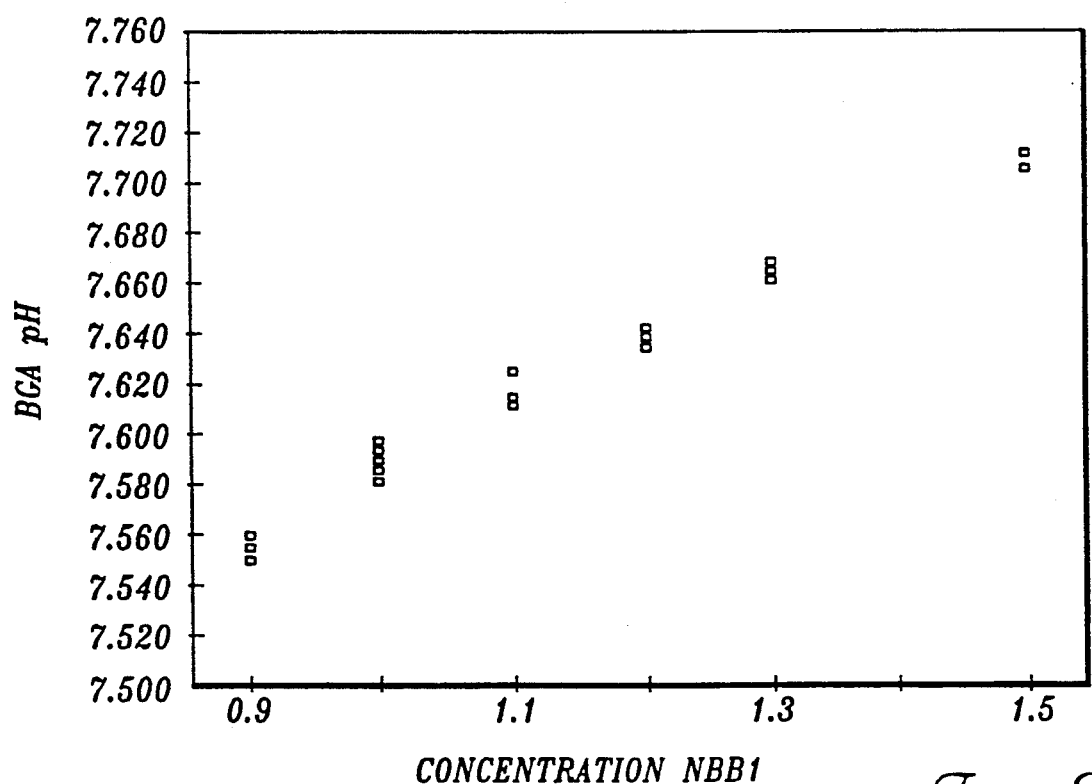
FIG. 8 is a graph that shows the increase in apparent pH recorded by a blood gas analyzer in different concentrations of a "defective" calibration solution, i.e., made up to mimic a pH 7.6 solution that has undergone evaporative loss and thus has experienced an increase in the buffer concentration.

The results presented in FIG. 7 (for the pH 7.2 set of buffers) and FIG. 8 (for NBB1, pH 7.6 set of buffers) show that as the concentration of all the constituents in NBB1 increased (i.e., from $0.9\times$ to $1.5\times$ NBB1), there was a corresponding significant increase in the apparent pH measured by the BGA with more than a 0.2 pH unit increase (FIG. 7) and 0.1 unit increase (FIG. 8) being observed from $1.0\times$ to $1.5\times$ NBB1.

This magnitude of error in pH is unacceptable for use in a blood gas pH catheter because a variation of 0.1 units in blood pH could indicate a highly significant underlying change in a patient's physiological status; particularly if following a general downward or upward trend with time. Thus, if buffer concentration were the only physical change affecting pH calibration of the sensor, the above-described phosphate-carbonate buffer would appear to be of limited value as a calibration solution if evaporative loss could not be carefully controlled during all phases of preparation, packaging, and use of the solution.

Figure 9:
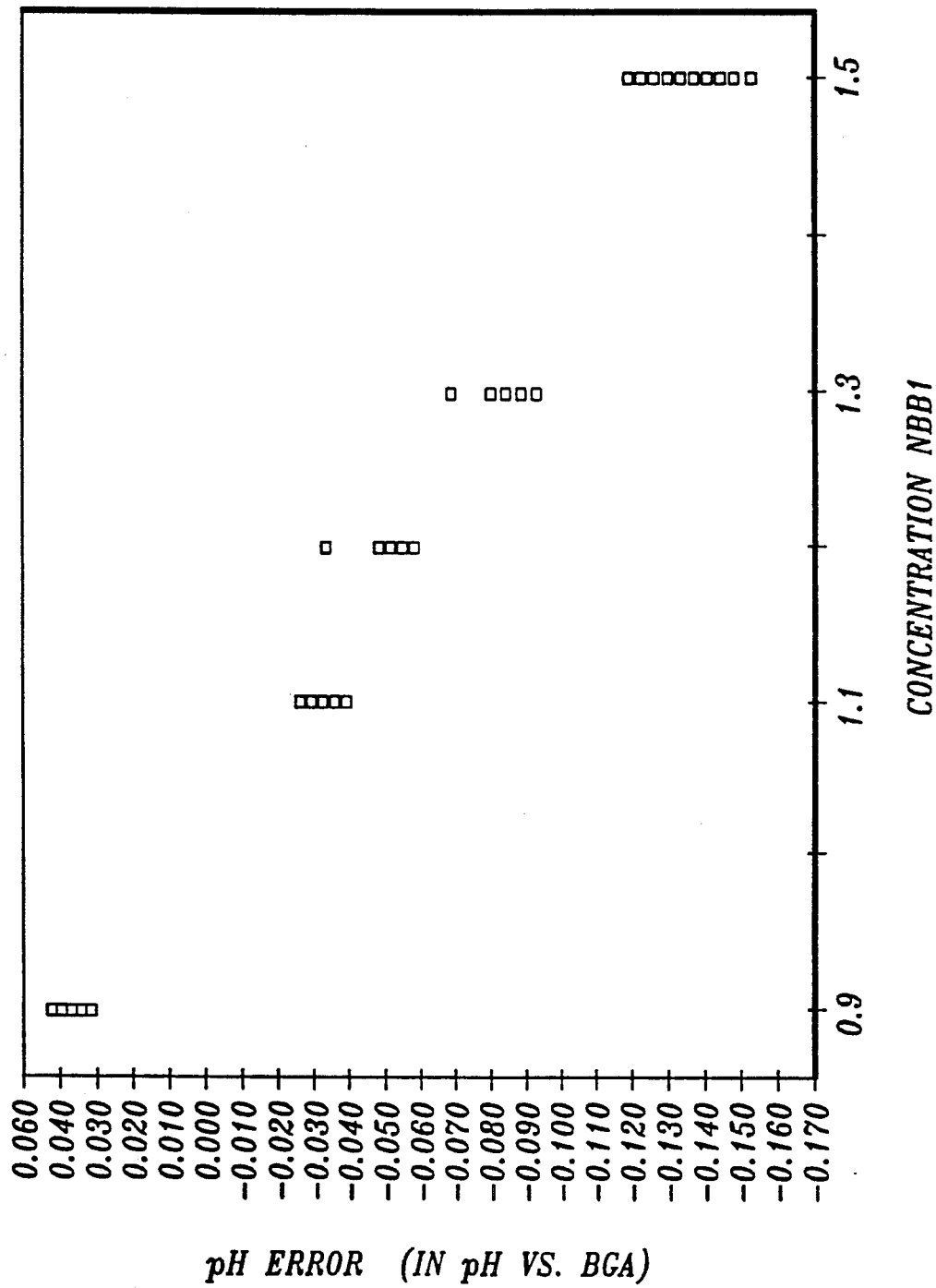
FIG. 9, depicts in graphic fashion the pH error resulting from equilibrating and calibrating a probe sensor component in "defective" calibration solutions containing a predominant anion in the solution to compensate for changes in the buffer composition, e.g., those that might occur during ETO sterilization or evaporation of the solution.

However, in contrast to expectations, when sensor components calibrated in $1.0\times$ NBB1, pH 7.2 or pH 7.6 were placed in $0.9\times$ to $1.5\times$ NBB1 solutions, the sensors recorded a pH of approximately 7.2, irrespective of the ionic composition of the buffer. The error recorded by the sensors (i.e., the value recorded by the sensor—the BGA measured value=error) in these experiments is presented in FIG. 9, which summarizes the cumulative values recorded in the error measurements for the NBB1, pH 7.2 and NBB1, pH 7.6 sets of buffers as a function of NBB1 concentration.

Figure 10:
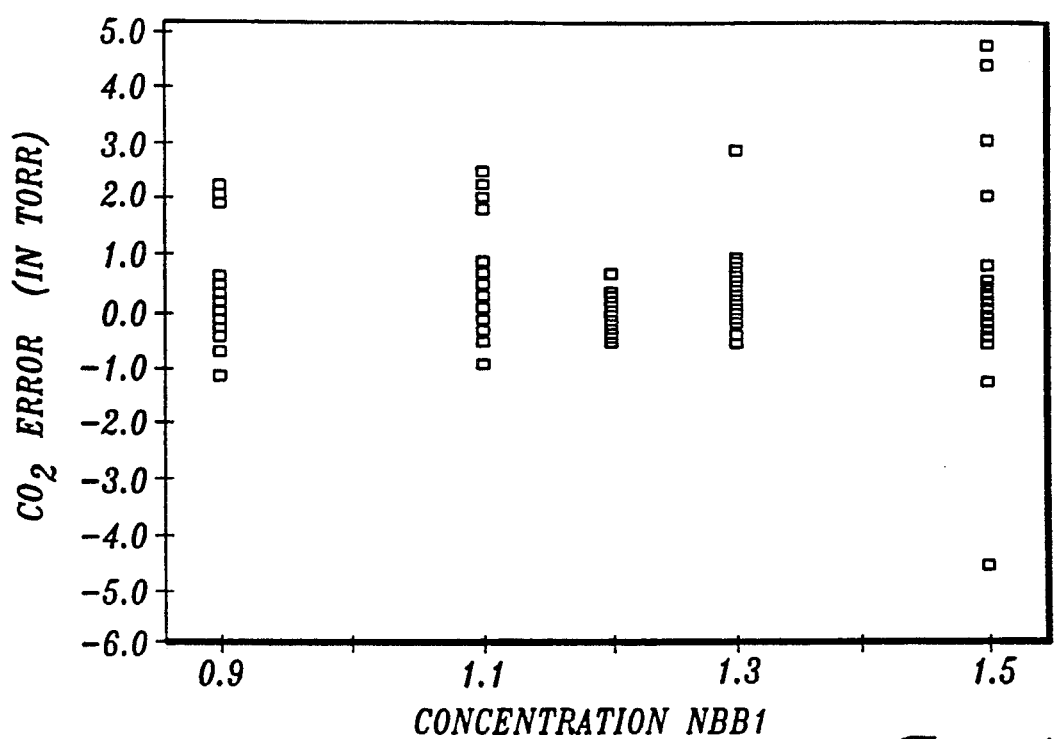
FIG. 10 is a graph, which depicts the lack of $pCO_2$ error resulting from equilibrating and calibrating a probe sensor in "defective" calibration solutions containing a predominant anion to compensate for changes in the buffer composition.
Figure 11:
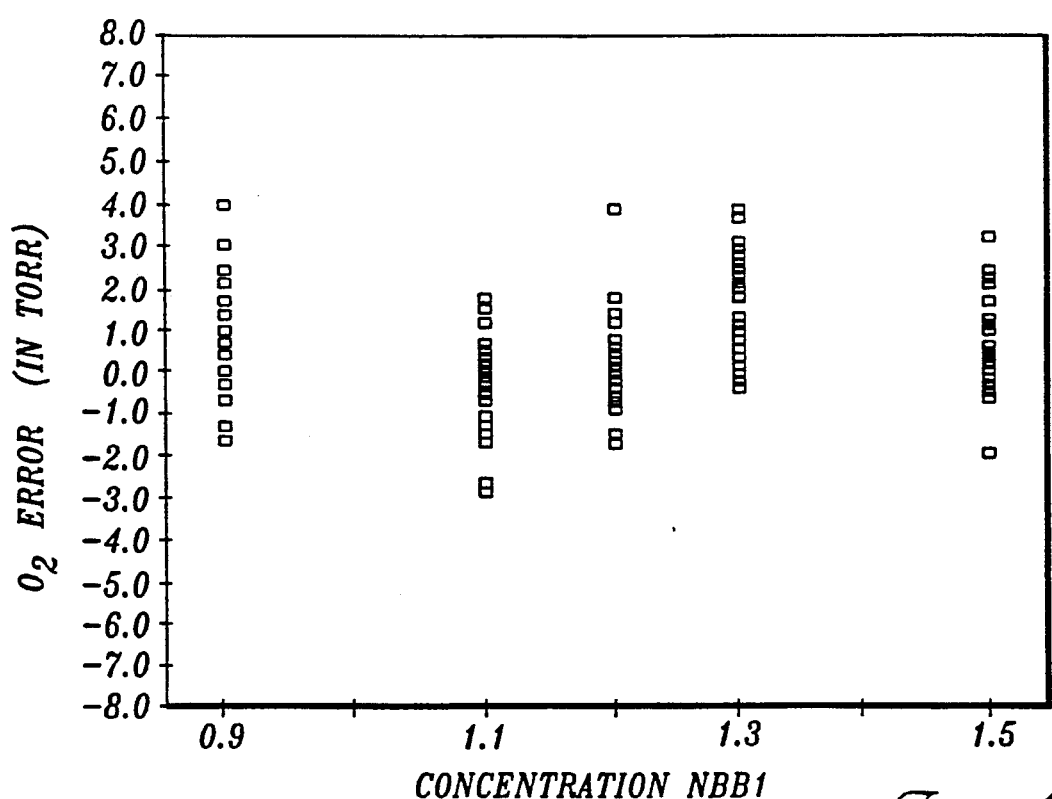
FIG. 11 is a graph which depicts the lack of $pO_2$ error resulting from equilibrating and calibrating a probe sensor in "defective" calibration solutions containing a predominant anion to compensate for changes in the buffer composition.

To determine the effects of evaporative loss on $pO_2$ and $pCO_2$ measurements, additional values were recorded in the same experiment (above). The results presented in FIGS. 10 and 11 show the values recorded for the error measurements of $pCO_2$ and $pO_2$ at $0.9\times$–$1.5\times$ NBB1, respectively.

Surprisingly, the changes in buffer concentrations of the calibration solutions also did not significantly alter the sensor measurement of $pCO_2$ and $pO_2$ measurements. The error in $pCO_2$ was less than 3 torr up to $1.3\times$ NBB1. While greater scatter in the error values was recorded at $1.5\times$ NBB1, the error was still less than 5 torr and within an acceptable range of variation for use in patient monitoring (FIG. 11). Similarly, error values for $pO_2$ were less than 4 torr and within acceptable limits. Since it is known that the partial pressure of a gas in a liquid is a complex function of at least electrolyte concentration and number of cations and anions (see the Nernst equation) and temperature, atmospheric pressure, molecular mass of the gas (see Charles/Gay-Lussac Law) it was considered highly fortunate that the solution chemistry of the calibration solution (i.e., presence of a predominant anion, two cations, and a mixed phosphate carbonate buffer system) as it interacts with the chemistry of the sensor allows sufficient flexibility to encompass use of calibration solutions that may have undergone changes due to evaporative loss (e.g., during calibration or storage).

While these experimental results suggested that changes in calibration solutions might affect the measurements of pH by a BGA, it was not clear how ignoring BGA-calibration and using a potentially "defective" calibration solution for hydrating and calibrating a sensor might affect the subsequent readings recorded by the sensor. Therefore, a study was conducted to determine how hydrating a sensor and then precalibrating it in a "defective" $1.0\times$, $1.1\times$, $1.25\times$, or $1.5\times$ NBB1 solution might affect subsequent measurements recorded by the sensor in a proper (NBB1, pH 7.6 or NBB1, pH 7.2; BGA pre-confirmed calibrated solution). For this study, several sensor probes in a transfer block were properly hydrated for 7–30 days in the concentrated ("defective") NBB1 solutions, and then precalibrated in the same "defective" solution before testing for pH error (as described above) by moving the probes between two different MPEVs, the first containing a BGA-confirmed calibrated solution of $1.0\times$ NBB1, pH 7.2 and in nominal 8.3% $CO_2$, 8.3% with 83.4% $N_2$, and the second containing the BGA-confirmed calibration solution of $1.0\times$ X NBB1, pH 7.6 and in nominal 2.8% $CO_2$, 21% $O_2$ and 76.2% $N_2$. The results presented in Table 1 show that sensors hydrated and precalibrated in "defective" solutions will still perform within acceptable limits for errors in measuring pH, $pO_2$ or $pCO_2$:

TABLE 1

The Effect of Hydration Buffer Composition on the Subsequent Error Recorded in pH, $pO_2$ and $pCO_2$ Measurements.

| NBB1 Hydration Buffer | pH 7.6 | pH 7.2 |
|---|---|---|
| | Mean pH Error Recorded* | |
| 1.0X | 0.004 ± 0.005 | 0.005 ± 0.005 |
| 1.1X | 0.009 ± 0.005 | 0.007 ± 0.008 |
| 1.25X | 0.011 ± 0.004 | 0.009 ± 0.008 |
| 1.5X | 0.02 ± 0.009 | 0.024 ± 0.008 |
| | Mean $pO_2$ Error Recorded* | |
| 1.0X | −0.932 ± 1.977 | N.D. |
| 1.1X | −0.74 ± 1.78 | N.D. |
| 1.25X | −0.126 ± 1.71 | N.D. |
| 1.5X | −0.8 ± 1.62 | N.D. |
| | Mean $pCO_2$ Error Recorded* | |
| 1.0X | −0.559 ± 0.133 | 0.555 ± 0.77 |
| 1.1X | −0.45 ± 0.59 | 1.15 ± 1.26 |
| 1.25X | −0.564 ± 0.542 | 1.18 ± 0.91 |
| 1.15X | −0.26 ± 0.5 | −0.27 ± 0.76 |

*Error, mean ± standard derivation, recorded in NBB1, 1.0X at pH 7.6 or pH 7.2; pH error in pH units; $pO_2$ and $pCO_2$ error in torr; N.D.—not determined in this experiment.

These results suggest an apparent lack of dependence of the probes upon the buffer compositions used for hydration and precalibration in this experiment. Thus, overall the results indicate that a sensor probe calibrated by ignoring the absolute pH value of the solution (i.e., as it might be determined in a BGA) does not result in an improperly calibrated sensor component and monitoring instrumentation. The results presented in Table 1 also show that the $pO_2$ and $pCO_2$ measurements in this experiment were fortunately independent of the concentration of NBB1 used in the hydration and calibration independent of the concentration of NBB1 used in the hydration and calibration buffers for the sensor probes, i.e., ignoring the BGA values for the calibration solution did not exert an effect on the values recorded by the sensor for $pO_2$ or $pCO_2$.

Considering the unexpected nature of the findings, additional studies were conducted to evaluate the possible solution chemistry responsible for the effect. The calibration/hydration solution was formulated to have a chloride ion concentration similar to the physiological milieu in blood, i.e., 105 millimolar, above, and an osmolality similar to blood, i.e., approximately 300 milliosmoles. To investigate the solution chemistry responsible for the effects on the sensor membrane, additional amounts of each constituent in $1.0\times$ NBB1 were added to each of a large series of test buffers, e.g., test buffers with additional sodium chloride, bicarbonate, or phosphate. As a positive control for the pH error observed previously (above, FIG. 9), a buffer was also prepared with additional amounts of all the constituents in NBB1 (i.e., similar to the $1.1\times$–$1.5\times$ NBB1, above). The magnitude of the pH error (or $pO_2$ or $pCO_2$ error) contributed by each additional millimole of anion (or NBB1) was determined using a sensor precalibrated in a BGA-confirmed calibration solutions of $1.0\times$ NBB1, pH 7.6 or pH 7.2 (as above).

The results presented in Table 2 show that each additional millimole of chloride ions caused a change in pH measurement of −0.00266/millimole, compared with a pH change of −0.00028/millimole of all the negative ions in NBB1 (i.e., there are approximately 10 species of negative ions generated by the chemical constituents of the calibration solution). Thus, the pH change caused by each millimole of chloride was approximately 10- fold greater than that caused by each millimole of all the other negative anions in NBB1; chloride caused nearly 4 times more pH change per millimole than any other single anionic constituent (i.e., phosphate or bicarbonate); and, no other single constituent in NBB1 contributed as significantly to the observed pH change in sensor measurements as chloride.

TABLE 2

The Effect of Each Additional Millimole of Negative Ions Contributed by the Buffer Constituents on the Change Recorded in pH, $pO_2$ and $pCO_2$ Measurements.

| Buffer Constituent | Mean Change Recorded/ Millimole Negative Ions* | | |
|---|---|---|---|
| | $pH^a$ | $pCO_2^b$ | $pO_2^b$ |
| NBB1 (All)$^c$ | −0.00028 ± .00027 | .00 ± .00 | .00 ± .00 |
| Chloride | −0.00266 ± .00032 | .00 ± .02 | .00 ± .06 |
| Bicarbonate | −0.00023 ± .00005 | −0.02 ± .01 | −0.00 ± .01 |
| Phosphate | −0.00067 ± .00110 | 0.00 ± .06 | 0.01 ± .07 |

*Change, mean ± standard deviation, recorded in 1.0X NBB1 at pH 7.6 or 7.2 and mean calculated for the cumulative results;
$^a$pH, pH units of change per millimole of constituent added to 1.0X NBB1;
$^b$$pO_2$ and $pCO_2$, torr units of change per millimole of constituent added to 1.0X NBB1.
$^c$NBB1 (All), total mean change calculated per each millimole of negative ions added to 1.0X NBB1.

Thus, the results in Table 2 suggest that increasing chloride anion concentration in a calibration buffer can decrease the apparent pH recorded by the probe sensor. In contrast, the previous results presented in FIGS. 7 and 8 show that increasing the concentration of all the constituents in the calibration buffer causes an apparent increase in pH recorded by the probe sensor. The net effect of the increase (FIGS. 7 and 8) and decrease (Table 2) in pH apparently cancels each other out and leads to the surprising properties of the calibration solution shown in results presented in Table 1.

Unexpectedly, it was found in other studies that ETO sterilization of a foil-wrapped container of prepartion solution created contaminants which could potentially alter the pH of such a preparation solution. In particular, it was found that ETO reacted with $H_2O$ and NaCl forming ethylene chlorohydrin and NaOH. The sodium hydroxide generated in this manner can potentially shift the pH of a calibration solution toward a more basic pH. High barrier overwrap packaging was particularly prone to this potential error because the enclosure retained the ETO rather than letting it de-gas into the atmosphere. Fortunately, the preparation solution of the invention is a rather strong buffer which tolerates contaminants produced in the sterilization process. The preferred embodiment detailed in the composition, above, allowed commercial ETO sterilization with only a shift of 0.015 to 0.025 pH units. The composition of preparation solution of the invention allows this favorable result. The use of halogens other than chloride, or of nonbuffered solutions, or less well buffered solutions would allow contaminants to form in the preparation solution which could be deleterious to the sensor component of the blood gas catheter.

Other methods for hydrating and calibrating a sensor membrane of a fiber optic catheter in a controlled atmosphere are anticipated using the aqueous buffer solution containing a predominant chloride anion which is an aspect of the invention, e.g., in a sealed chamber, envelope or packaging device. It will also be recognized that creating a constant gaseous environment for storage and incubation purposes is not necessary if the delivery device itself is gas-impermeable and contains the constant gaseous environment for calibration.

In a preferred embodiment the gaseous atmosphere for "gassing" the calibration to two desired calibration points are gas mixture of nominal 8.3% $CO_2$, 8.3% $O_2$, and 83.4% $N_2$, for a desired pH approximating a desired pH value of 7.2, and nominal 2.8% $CO_2$, 21% $O_2$, and 76.2% $N_2$ for approximating a desired pH value of pH 7.6. It is desirable that the $CO_2$ and $O_2$ in these respective gases be controlled within a range of +/−0.03%. It is also desirable that the barometric pressure within the equilibration chamber (e.g., an MPEV) be maintained within a measured range of barometric pressure, since pressure controls the volume of a gas and the partial pressure of gas in a liquid. In another preferred embodiment it is desirable that the barometric pressure in the equilibration chamber be controlled over +/−4 torr during the calibration period.

The aqueous buffer solution which is an aspect of the invention anticipates buffering composition with differing amounts of potassium and sodium phosphate and sodium bicarbonate sufficient to achieve a desired pH range in the calibration solution after gassing to achieve a desired calibration point.

Those skilled in the art will recognize that gassing the solution of the invention with a gas mixture containing $CO_2$ drives the equilibrium toward dissociation of dibasic sodium phosphate with formation of monobasic sodium phosphate and sodium bicarbonate: i.e., the greater the $CO_2$ concentration the lower the pH of the solution. It will also be apparent that the preparation solution of the invention has amounts of sodium and potassium phosphate, and sodium bicarbonate sufficient to provide buffering capacity to compensate for contaminants, e.g., ETO sterilization residuals (above), which could potentially influence the pH of the solution either during sterilization or storage in polymeric containers, e.g., polycarbonate or polyvinyl packages, which may "leach" ionic contaminants into the solution during storage. Those skilled in the art will recognize that if the amounts of sodium phosphate, potassium phosphate, and sodium bicarbonate in the preparation solution of the invention required to achieve a desired calibration point within a desired range of pH values in a gaseous atmosphere containing at least $O_2$ and $CO_2$ is readily determined empirically, e.g., by preparing, packaging, sterilizing, and storing a test solution and monitoring the performance of the solution in calibrating sensor components and monitoring instruments in a manner similar to that described above. The inclusion of a predominant anion in these calibration solutions (i.e., chloride anion), provides anionic compensation for the sensor membrane during hydration and calibration. In a preferred example, the buffer as initially prepared has a pH of approximately 7.3-7.4 so that a sensor probe stored in the buffer will not be affected in a deleterious manner by pH, and a controlled gaseous atmosphere is then used in gassing the calibration to desired calibration points of approximately pH 7.2 and 7.6, i.e., in a solution which has not been affected by evaporative loss or contaminants. In other embodiments the calibration solution and process of calibrating the sensor component and monitoring instrumentation as provided by the invention offers other calibration points (e.g., of different pH, $pO_2$, $pCO_2$, etc.) such as will be readily recognized by those skilled in the art to be achieved by theoretical and empirical (e.g., experimental) means.

While preferred embodiments of the invention have been illustrated and described, it will be appreciated that various changes can be made herein without departing from the spirit and scope of the invention.

The embodiments of the invention in which an exclusive property or privilege is claimed are defined as follows:

1. A method of equilibrating a sensor component membrane of a fiber-optic catheter useful for measuring at least one analyte other than chloride in blood to determine pH, $pO_2$, or $pCO_2$ in a blood sample, comprising the step of contacting the sensor component membrane with an aqueous buffer solution containing chloride at a level substantially equal to the level found in blood, for a period of time sufficient to equilibrate the sensor membrane so that an ionic gradient is prevented from forming across the sensor component membrane when the sensor component membrane is contacted with the blood sample.

2. The method of claim 1, wherein the aqueous buffer solution comprises bicarbonate and phosphate ions.

3. The method of claim 1, wherein the aqueous buffer solution consists essentially of:
   0.916 g/l potassium phosphate,
   3.007 g/l sodium phosphate,
   6.136 g/l sodium chloride, and
   1.848 g/l sodium bicarbonate, in aqueous solution.

4. A method of equilibrating and calibrating a sensor component membrane and monitoring instrumentation of a fiber-optic catheter useful for measuring at least one analyte other than chloride in a blood sample comprising the steps of:
   contacting the sensor component membrane with a first aliquot of an aqueous buffer solution containing chloride at a level substantially equal to the level found in said blood, for a period of time sufficient to equilibrate said sensor component membrane so that an ionic gradient is prevented from forming across the sensor component membrane when the sensor component membrane is contacted with a blood sample;
   exposing a second aliquot of the aqueous buffer solution to a controlled gaseous atmosphere to achieve a controlled calibration point value;
   contacting the sensor component membrane with the second aliquot of the aqueous buffer solution at the controlled calibration point value; and,
   contacting the sensor component membrane with the blood sample and determining that an ionic gradient does not form across the sensor component membrane.

5. The method of claim 4, wherein the controlled calibration point value is selected from a pH value within the range of pH 7.2 to pH 7.6.

6. The method of claim 5, wherein the controlled calibration point value is a pH value of 7.2.

7. The method of claim 5, wherein the controlled calibration point value is a pH value of 7.6.

8. The method of claim 4, wherein the controlled gaseous atmosphere comprises $CO_2$, $O_2$ and $N_2$.

9. The method of claim 8, wherein the controlled gaseous atmosphere comprises 8.3% $CO_2$, 8.3% $O_2$ and 83.4% $N_2$.

10. The method of claim 8, wherein the controlled gaseous atmosphere comprises 2.8% $CO_2$, 21% $O_2$ and 76.2% $N_2$.

11. The method of claim 4, wherein the aqueous buffer solution consists essentially of:
    0.916 g/l potassium phosphate,
    3.007 g/l sodium phosphate,
    6.136 g/l sodium chloride, and
    1.848 g/l sodium bicarbonate, in aqueous solution.

12. A method of equilibrating and calibrating a sensor component membrane and monitoring instrumentation of a fiber optic catheter useful for measuring at least one analyte other than chloride in blood, comprising the steps of:
    contacting the sensor component membrane with an aqueous buffer solution containing chloride at a level substantially equal to the level found in said blood, for a period of time sufficient to equilibrate said sensor component membrane so that an ionic gradient is prevented from forming across the sensor component membrane when the sensor component membrane is contacted with a blood sample; and
    exposing the aqueous buffer solution and sensor component membrane to a controlled gaseous atmosphere under conditions sufficient to achieve a controlled calibration point value.

* * * * *

UNITED STATES PATENT AND TRADEMARK OFFICE
CERTIFICATE OF CORRECTION

PATENT NO. : 5,328,848            Page 1 of 2
DATED       : July 12, 1994
INVENTOR(S) : Fong et al.

It is certified that error appears in the above-indentified patent and that said Letters Patent is hereby corrected as shown below:

| COLUMN | LINE | |
|---|---|---|
| [75] (Col. 1) | Inventors | "Snohemish" should read --Snohomish-- |
| [56] (Col. 2) | Ref. Cited (U.S. Pat. Docs.) | Insert --4,163,734 08/1979 Sorensen, S.K. et al. 252/408-- |
| [56] (Col. 2) | Ref. Cited (U.S. Pat. Docs.) | Insert --4,363,633 12/1982 Christiansen, T.F. 436/19-- |
| [56] (Col. 2) | Ref. Cited (Publications) | Insert --"Scientific Tables", Eds. K. Diem and C. Lentner, Seventh Edition, Ciba-Geigy Corporation, Basle, Switzerland, 1973. p.562.-- |
| 1 | 10 | "§ 120." should read --§ 120 and 121.-- |
| 3 | 33 | "the" should read --The-- |
| 11 | 47 | "an situ" should read --an in situ-- |

UNITED STATES PATENT AND TRADEMARK OFFICE
CERTIFICATE OF CORRECTION

PATENT NO. : 5,328,848

DATED : July 12, 1994

INVENTOR(S) : Fong et al

It is certified that error appears in the above-indentified patent and that said Letters Patent is hereby corrected as shown below:

| COLUMN | LINE | |
|---|---|---|
| 12 | 25 | "means" should read --mean-- |
| 15 | 61 | "8.3% with" should read --8.3% $O_2$ with-- |

Signed and Sealed this

Fifteenth Day of November, 1994

Attest:

BRUCE LEHMAN

Attesting Officer   Commissioner of Patents and Trademarks